(12) United States Patent
Schuchmann et al.

(10) Patent No.: US 8,210,060 B2
(45) Date of Patent: Jul. 3, 2012

(54) COLUMN PRESS FOR QUALITY ANALYSIS

(75) Inventors: Martin Schuchmann, Mannheim (DE); Hermann Herbel, Harthausen (DE)

(73) Assignee: Rhein Chemie Rheinau GmbH, Mannheim (DE)

( * ) Notice: Subject to any disclaimer, the term of this patent is extended or adjusted under 35 U.S.C. 154(b) by 344 days.

(21) Appl. No.: 12/577,348

(22) Filed: Oct. 12, 2009

(65) Prior Publication Data

US 2010/0175489 A1    Jul. 15, 2010

(30) Foreign Application Priority Data

Oct. 16, 2008    (DE) .......................... 10 2008 042 906

(51) Int. Cl.
*G01N 33/00*    (2006.01)
(52) U.S. Cl. ........................................ 73/866
(58) Field of Classification Search .................. None
See application file for complete search history.

(56) References Cited

U.S. PATENT DOCUMENTS

2009/0082510 A1*  3/2009  Miyamori et al. ............ 524/429
2009/0311453 A1  12/2009  Mihan et al.

FOREIGN PATENT DOCUMENTS

DD           159718 A1     3/1983
DE     102004048098 A1     4/2006

* cited by examiner

*Primary Examiner* — Robert R Raevis
(74) *Attorney, Agent, or Firm* — Nicanor A. Kohncke

(57) ABSTRACT

The invention relates to a method and equipment for the testing of quality of polymer-bound rubber additives.
According to the method, a polymer-bound rubber additive (3) is mixed with an EPDM masterbatch (2). The resultant test mixture (5) is forced through a test sieve (10), and the number of undispersed particles (14) removed by sieving is determined.

9 Claims, 3 Drawing Sheets

COLUMN PRESS FOR QUALITY ANALYSIS

CROSS REFERENCE TO RELATED PATENT APPLICATIONS

The present patent application claims the right of priority under 35 U.S.C. §119 (a)-(d) of German Patent Application No. DE 10 2008 042 906.6 filed on 16 Oct. 2008.

The invention relates to a method and equipment for the testing of quality of polymer-bound rubber additives. The testing of quality of a polymer-bound rubber additive takes place indirectly via testing of a test mixture produced, comprising the polymer-bound rubber additive. An example of polymer-bound rubber additives of this type is obtainable commercially as Rhenogran®. Rhenogran® encompasses at least one rubber additive and at least one polymeric binder. Examples of rubber additives that can be used are sulphur, vulcanization accelerators such as MBTS, antioxidants such as MBI and also activators such as zinc oxide.

The expression Rhenogran® covers by way of example crosslinking agents supplied for the purpose of producing an elastomer from a rubber with the aid of the crosslinking agent. "Rhenogran® S-80" is a crosslinking agent of this type, composed of 80% of sulphur and 20% of polymer binders.

Another example from the Rhenogran® product range is called Rhenogran® MBI-80 and is based on the antioxidant MBI. Rhenogran MBI-80 comprises 80% of active ingredient MBI and 20% of binder. The active ingredient MBI is mercaptobenzimidazole.

Rhenogran® additives are used by way of example for the production of products composed of rubber.

As a function of the quality of a polymer-bound rubber additive, there can be undispersed particles, i.e. visible alterations in the material, in the final vulcanized product. There can be technical defects associated therewith. The smaller the number of undispersed particles present in the final product, the higher the quality of the polymer-bound rubber additive.

The publication DD 159718 discloses a method for the production of blends composed of butadiene-acrylonitrile rubbers and polyvinyl chloride, which are produced by mixing of butadiene-acrylonitrile lattices and polyvinyl chloride lattices. According to the said publication, undispersed particles can form in the final solid product by virtue of entrained precipitant particles, which reduce product quality and lead to difficulties during further processing. The publication DE 10 2004 048 098 A1 also discloses that undispersed particles reduce product quality.

The publication DE 10 2005 019 395 A1 discloses that the mix quality of a polyethylene powder obtained directly from a reactor can be tested by assessing thin sections (microtome sections) of a specimen under an optical microscope. As the number of inclusions known as undispersed particles becomes fewer and as these become smaller, the mix quality of a polymer becomes better. The mix quality of a polymer is determined quantitatively to ISO 13949. According to the test specification, a microtome section composed of a specimen of the polymer is prepared, a counting method is used to determine the number and size of the inclusions, and a classification for the mixed quality of the polymer is determined in accordance with a defined evaluation system.

It is an object of the invention to provide a method which can reliably test the quality of a polymer-bound rubber additive, and also equipment for carrying out the method.

DETAILED DESCRIPTION OF THE INVENTION

Figure 1:
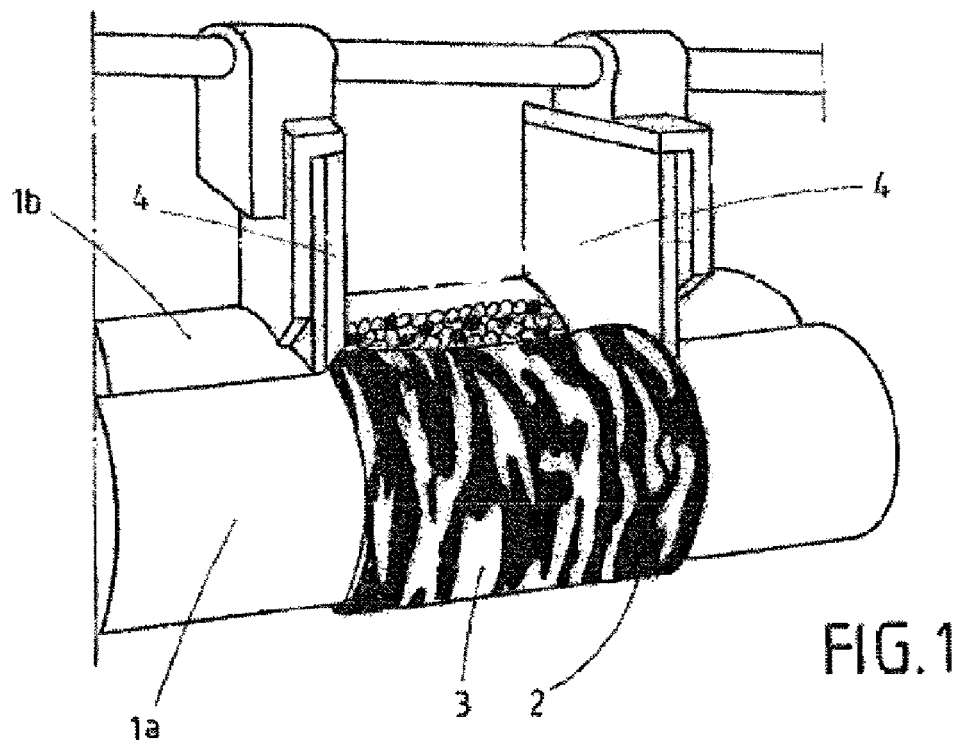
FIG. 1 schematically illustrates a temperature-controlled double-rolling apparatus system.

In order to achieve the object, a test mixture is produced, encompassing the polymer-bound rubber additive to be tested and a test masterbatch. The test masterbatch preferably comprises one or more rubbers, carbon black, pale-coloured fillers, plasticizer oil, crosslinking activator and/or processing aids. Production of the test mixture in particular uses polymer-bound rubber additive—for example 100 g—and black EPDM masterbatch—for example 300 g. Black EPDM masterbatch comprises not only the polymer EPDM, i.e. ethylene-propylene-diene rubber, but also further additions, and specifically and in particular considerable amounts of carbon black, and also oils as plasticizer. The aim of using a test masterbatch is to provide the best possible simulation of a material actually used, and thus to permit reliable testing of quality. This aim is achieved by way of example via provision of an EPDM masterbatch as test masterbatch. Instead of EPDM, it is possible to use rubbers such as natural rubber (NR) or other synthetic rubbers such as styrene-butadiene rubber (SBR), butadiene rubber (BR), polyisoprene rubber (IR), butyl rubber (IIR), nitrile-butadiene rubber (NBR) and hydrogenated NBR (HNBR), polychloroprene rubber (CR), ethylene-propylene rubber (EPM), acrylate rubbers (AEM, ACM), fluoro rubber (FKM), epichlorohydrin rubber (ECO), ethylene-vinyl acetate rubber (EVM) or a mixture of the abovementioned rubbers.

The polymer-bound rubber additive is first incorporated by mixing into a test masterbatch, in particular into black EPDM masterbatch, and the same procedure is specifically used here for every quality test. The polymer-bound rubber additive is preferably incorporated by mixing into the test masterbatch, for example the black EPDM masterbatch, on a temperature-controlled roller with a defined width of the nip. The roller is in particular temperature-controlled, in order to obtain viscosities appropriate for processing. Temperatures of from 50 to 80° C. are generally suitable for the temperature-control process and are specifically and particularly suitable in the case of black EPDM masterbatch.

There are four parameters which affect a mixing result achieved by means of a temperature-controlled roller. One parameter is the temperature to which a roller is temperature-controlled. A second parameter is the width of the nip, and a third parameter is the mixing time. A fourth parameter is the handling method used to feed the polymer-bound rubber additive and the test masterbatch. The said four parameters are not altered for the conduct of quality-control procedures, the aim of this being to achieve comparable results which can give an immediate conclusion about the quality of the respective test mixture studied. For this reason, the feed procedure, inter alia, is always the same, the aim being to avoid differences in results due to handling procedures which are not comparable.

The prescribed width of the nip has a decisive effect on the shear energy introduced into the mixture. The width of the nip is selected in such a way as to give a desired dispersion result.

Once the width of the nip has been selected in this way it is retained for subsequent studies.

Once the prescribed mixing time has expired, the mixture is forced through a sieve (hereinafter also termed test sieve), for example with the aid of a screw. An extruder suitable for this purpose, with sieve and screw, is supplied by way of example by GÖTTFERT Werkstoff-Prüfmaschinen GmbH, Buchen, Germany. The extruder encompasses a feed screw, by which the test mixture is transported to a sieve and forced through the sieve. Once the test mixture has been completely extruded, the sieve, also termed strainer attachment, is disassembled. The sieve cake retained in the strainer attachment is removed, i.e. released from the sieve, and examined under a microscope, by using a counting method to determine the size and number of undispersed particles. The greater the number of undispersed particles found, and the greater their size, the poorer is the result. The evaluation procedure in particular uses standardized evaluation methods. In the context of this type of standardized evaluation method, categories are prescribed and specifically and particularly subdivided according to the size of the undispersed particles. By way of example, a first category can refer to undispersed particles whose size is from 75 µm to 175 µm, a second category can refer to undispersed particles whose size is from 175 µm to 250 µm, and a third category can refer to undispersed particles whose size is greater than 250 µm. By way of example, only a certain number of undispersed particles is permissible in each category. If this prescribed number is exceeded, the polymer-bound rubber additive does not, for example, comply with the quality requirements and does not pass onward for sale as originally intended.

Transport functions of this type usually use a screw in the prior art, since a screw has particularly good suitability for this type of function, for reasons mentioned below.

To permit feed of the test mixture to the input zone of a screw, the dimensions of the test mixture are first rendered suitable, for example by cutting to give strips. If the test mixture cools, the viscosity is then generally too high to permit transport of the test mixture and forcing of the mixture through a sieve, but a screw can specifically generate very large forces. The screw is therefore especially also temperature-controlled, with the aim of transferring heat to the test mixture over a large area. This in particular permits heating of the entire test mixture transported by the screw, since the counter-forces arising during the transport procedure cause a portion of the test mixture to flow backwards, the result being that the test mixture undergoes further mixing within the extruder, and the heat needed to obtain the desired viscosity is rapidly distributed. Frictional heat is also generated during this process, and makes a further contribution to avoiding any excessive rise in the viscosity of the test mixture.

Transport using a screw can be achieved without difficulty even when viscosity variations have to be overcome. If a variation causes the viscosity to rise locally, when a screw is used this can be compensated by reverse flow of material. Viscosity variations do not stop a screw or damage it.

Although, in terms of capability for carrying out the process, there are some important advantages attached to the reverse flow of material within an apparatus in which transport is effected via a screw, mixing of the mixture by the reverse flow process is unpredictable. The said mixing caused by transport using a screw alters the desired result in a non-reproducible and disadvantageous manner.

In one particularly preferred embodiment of the invention, the mixture is therefore forced, in a cylinder, by a piston, through a sieve which has been secured at one end of the cylinder.

It is true that transport of the mixture using piston and cylinder is problematic for a number of reasons. By way of example, it is not possible to achieve suitable temperature-control of the test mixture in order to avoid a rise in viscosity that then prevents transport, because when a cylinder together with piston is used, heat can only be conducted from the outside to the test mixture. For this reason alone, it is impossible to convey heat uniformly into the test mixture at an adequate rate. Once the test mixture is within the cylinder it is only transported, with no additional mixing due to reverse flow, and therefore there is none of the heat exchange which is associated with that process and which, in the case of an extruder, promotes the desired temperature-control of the test mixture.

There is then no possibility of compensating viscosity variations by increasing reverse flow of the material. Transport by means of piston and cylinder is therefore susceptible to stoppage, and to damage to the drive or to the sieve.

However, there is a significant advantage connected with transport in a cylinder. Since the test mixture is specifically not subjected to any additional mixing during transport, the result of quality control is not altered by any mixing due to transport.

Surprisingly, it has been found that the problems associated with transport by means of piston and cylinder can be solved. By way of example, when a cylinder is used the entire area of the base is available for charging a test mixture to the cylinder. It is therefore not then necessary to divide the test mixture into portions in the manner known from the prior art, for example to cut it into strips, in order to charge the test mixture to a transport apparatus (i.e. an extruder, for example). It is therefore preferable that the test mixture to be studied is suitably moulded in the manner of a cylinder and inserted into the cylinder. This can be done very rapidly, and the test mixture therefore undergoes very little cooling, and the viscosity does not therefore rise excessively at this juncture. It has been found that the test mixture thus charged to a cylinder can then be forced much more rapidly through the test sieve. A first reason for this is that no mixing then takes place during transport. Another difference from the extruder is that an increased transport rate does not lead to increased mixing during transport, with increase distortion of the result of quality control, and a resultant upward limit on transport rate. It has also been found that the possible processing velocities during the transport procedure do not cause the viscosity of a test mixture to rise to an extent that prevents relatively rapid transport. It has been found that the variations in viscosity are moreover then not so pronounced as to prevent transport at the desired or required rate.

In one embodiment of the invention, polymer-bound rubber additive is mixed, as described above, with the test masterbatch with the aid of a double-roll system. The resultant test mixture can finally be obtained in the form of a mat (milled sheet of mixture). The mat (milled sheet of mixture) can immediately be rolled to produce the desired cylindrical form. The desired cylindrical form can be obtained easily at the required rate, and the test mixture temperature-controlled via the roller does not therefore undergo excessive cooling. However, as an alternative to this it is also possible to use another mixing method and then, with the aid of a roller, to convert the test mixture first into the form of a mat and then into the form of a roll. However, this variant requires an additional operation. In any event, the said two embodiments can provide a particularly reliable method of overcoming the problems associated with transport by means of cylinder and piston.

If a cylinder with piston is used for the transport procedure, this also permits reduction of cleaning cost, since a cylinder with piston is not only easier to clean than a screw but is also less susceptible to contamination, because the scrapping action of the piston removes deposits on the inner walls of the cylinder.

The cylinder is generally vertical. The sieve which is then uppermost has a typical mesh width of 150 μm, while all of the sieves located thereunder serve as ancillary sieves and have a larger mesh width. A typical structure encompasses a perforated plate, which serves to prevent blocking. All of the undispersed particles larger than 150 μm are then retained in the sieve with mesh width 150 μm (the sieve with the smallest mesh width).

After this, there can be an ancillary sieve provided with mesh width 250 μm, underlying the 150 μm sieve. Following this, there can be an ancillary sieve with mesh width 500 μm, underlying the 250 μm sieve. Finally, there can be a perforated plate underlying all of the sieves.

The invention encompasses a method for the testing of polymer-bound rubber additives, according to which a polymer-bound rubber additive is mixed with a test masterbatch, in particular with an EPDM masterbatch, the resultant test mixture is forced through a test sieve, and the number of undispersed particles removed by sieving is determined.

In one embodiment of the method, the test mixture is forced through the test sieve (10) with the aid of a piston (7) and of a cylinder (6). In another embodiment of the method, a heated test mixture (5) is first converted to the form of a roll or of a cylinder, and the test mixture (5) thus moulded is inserted into a cylinder (6), and is forced through the test sieve (10) with the aid of a piston (7).

In another embodiment of the method, the test mixture is moulded using at least one roller (1, 1a) to give a mat. The mat is rolled up and, in rolled-up form (5), forced through the test sieve (10).

The invention also encompasses an embodiment of the method in which polymer-bound rubber additive (3) and test masterbatch (2) are mixed by means of a double-roll system (1, 1a).

The invention further provides an embodiment of the method in which a plurality of sieves and/or of plates (8, 9, 10) in the form of a sieve have been arranged adjacent to one another behind the test sieve (10), seen in the direction of pressure, and the mesh size of each of the sieves (8, 9, 10) here increases in the direction of pressure.

The invention encompasses an embodiment of the method in which a ring (11) has been arranged in front of the test sieve (10).

The invention also provides equipment for carrying out the method with a cylinder (6) and with a piston (7) conducted therein, with a plurality of sieves (8, 9, 10) at one end of the cylinder and with a ring adjacent to a sieve (10).

The invention encompasses an embodiment of the equipment where a sieve (10) has a mesh width of not more than 150 μm and the meshes of the sieves (8, 9) adjacent thereto towards the outside are greater.

The invention provides an embodiment of the equipment encompassing a double-roll system (1a, 1b) together with delimiter plates.

The size of the assemblies defines the possible amounts used for the testing procedure. The size of the cylinder limits the maximum amount.

An example is used below for further explanation of the invention, without any restriction of the invention thereto.

FIG. 1 shows a commercially available, temperature-controlled double-roll system, composed of two steel cylinders 1a and 1b arranged one behind the other. On the steel cylinders there is firstly EPDM masterbatch 2 and secondly a product from the Rhenogran® product range 3. The width of the nip between the two rollers is generally in the millimeter range, for example from 1 to 10 mm, preferably up to 3 mm. Once a nip width has been selected for the conduct of a quality-control procedure, this is also retained for subsequent quality-control procedures.

The EPDM masterbatch used (masterbatch No. 9-318 EPDM) had the following constitution:

| | | |
|---|---|---|
| Buna ® EPG 5450 | 100 | phr |
| N 550 carbon black | 90 | phr |
| Sillitin N 85 = | 50 | phr, silica with kaolinite, obtainable from Hoffman Mineral GmbH |
| Paraffin oil | 75 | phr |
| Active ZnO | 5 | phr |
| PEG 4000 | 2 | phr = polyethylene glycol 4000 obtainable from Brühl - Chemikalien Handel GmbH |
| Stearic acid | 1 | phr |
| Rhenosorb C/ Rhenofit C | 5 | phr = calcium oxide, obtainable from Rhein Chemie Rheinau GmbH |
| | 328 | phr |

Buna® is an ethylene-propylene-diene rubber, obtainable from LANXESS Deutschland GmbH, with ethylene content of 52±4% by weight and with Mooney viscosity ML of (1+4) 46±5 MU at 125° C.

The term phr ("parts per hundred rubber") is familiar to the person skilled in the art and gives the parts by weight in the constitution.

300 g of the EPDM masterbatch are weighed out and charged to the roller. 100 g of the respective Rhenogran product (e.g. Rhenogran TBzTD-70)=tetrabenzylthiuram disulphide, obtainable from Rhein Chemie Rheinau GmbH, are introduced in the form of granules. The granules are scattered into the material as soon as the masterbatch has reached a sufficient temperature and the viscosity is sufficiently low.

Above the rollers 1a, 1b, adjacent to these, there are two delimiter plates 4, the function of which is to prevent uncontrolled spread of the material 2, 3.

The mixing procedure is carried out manually by the following method. Using a knife, a person, by way of example, removes a section by making an oblique cut and replaces it at another point on the front roller 1a.

Once the incorporation and dispersion process has been carried out on the entire material 2, 3, the resultant test mixture has a homogeneous black colour. The test mixture is cut parallel to the axis of the rolls, and peeled away and rolled up in the shape of a cylinder. However, it is also possible that the test mixture which has been peeled away and rolled up, or the rolled-up milled sheet of the mixture, is again passed one or more times through the pair of rollers in an intermediate step, with resultant further homogenization. The test mixture then finally takes the form of a mat (milled sheet of the mixture), which is rolled up. The temperature of the said roll is then typically about 60° C.

Figure 2:
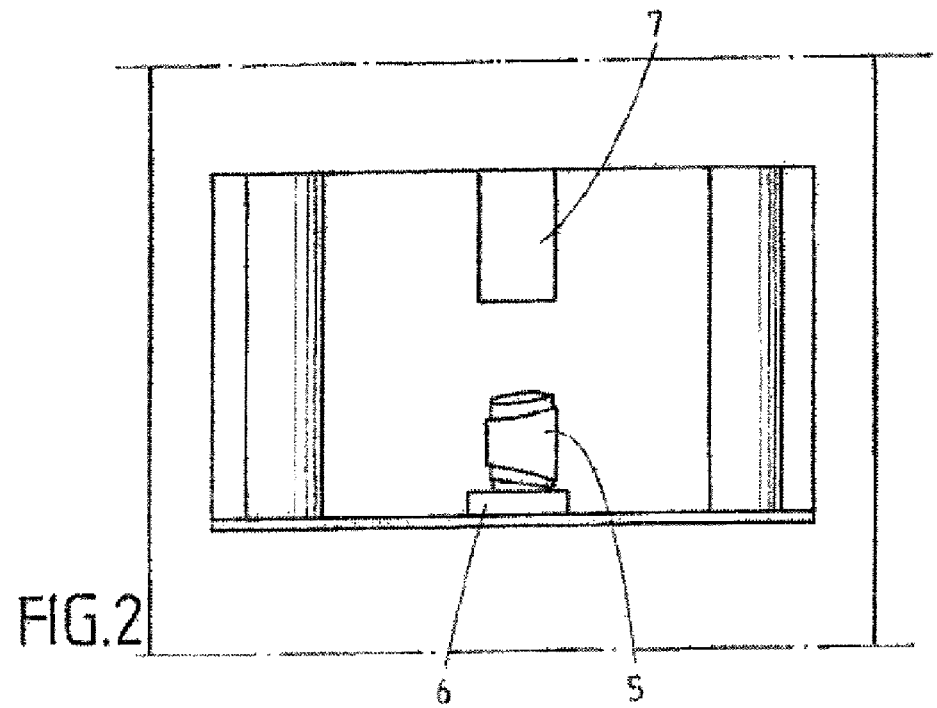
FIG. 2 schematically illustrates an apparatus having a cylinder capable of forcing a roll-shaped material produced with the use of the apparatus as shown in FIG. 1 through a sieve.

The resultant roll 5, the temperature of which is generally about 60° C., is inserted into a cylinder 6 provided for this purpose, as shown in FIG. 2. Using a piston 7 shown in FIG. 2, the roll-shaped test mixture 5 is forced through a sieve. The diameter of the cylinder shown is by way of example from 3 to 10 cm. The length of the cylinder is by way of example from 20 to 60 cm.

Figure 3:
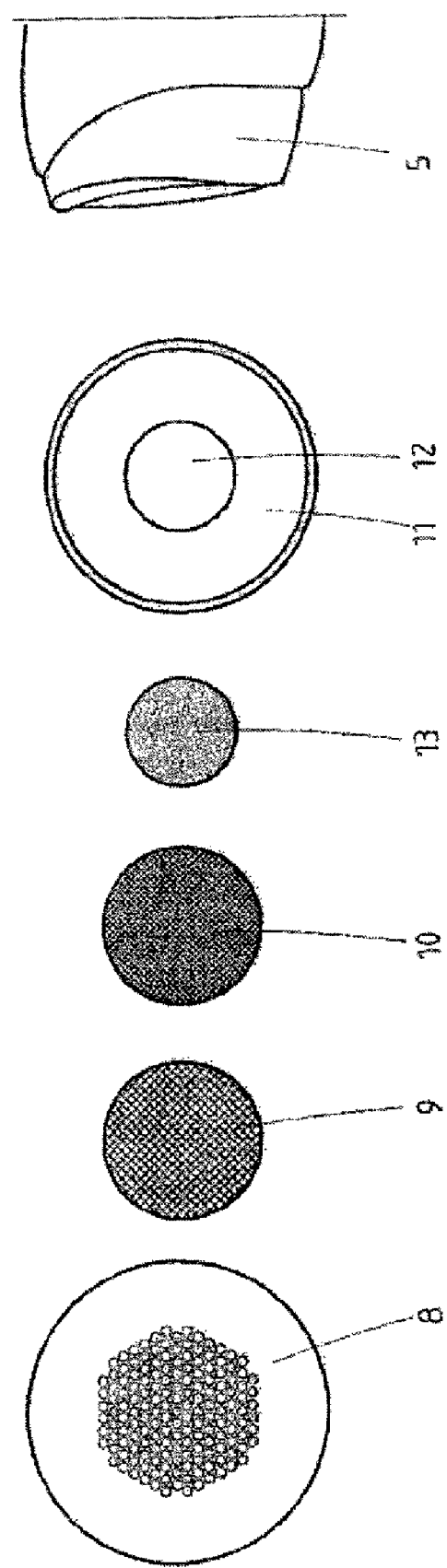
FIG. 3 schematically illustrates further views of the cylinder of FIG. 2.
Figure 5:
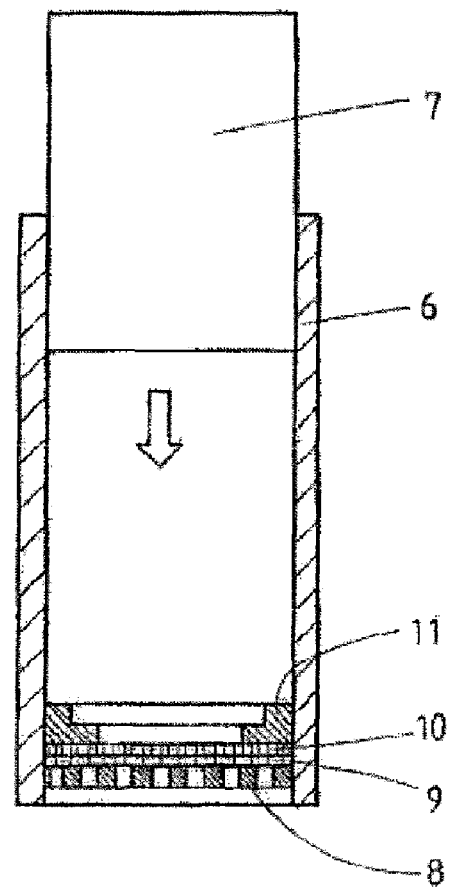
FIG. 5 schematically illustrates further views of the cylinder of FIG. 2.

FIGS. 3 and 5 illustrate the structure of the lower end of the cylinder, the end that encompasses a sieve. FIG. 5 shows a section of the structure.

The lower end has firstly been provided with a relatively thick plate 8 composed of steel in the form of a sieve, and this plate serves as first support for withstanding the pressures arising. The plate 8 has been provided with a plurality of relatively large holes. Above the plate 8 in the form of a sieve, a comparatively thin sieve 9 is placed, the mesh width of which can be about 500 µm, and which also serves as a support. The test sieve 10, likewise relatively thin, with mesh width of about 150 µm, then lies on the ancillary sieve 9. The mesh width of the test sieve 10 is generally selected in such a way that the meshes permit passage of the undispersed particles regarded as permissible. The ancillary sieve and the plates in the form of a sieve have meshes which are increasingly larger. The undispersed particles then removed by sieving are only those regarded as excessively large.

During the transport procedure, the test sieve 10 is exposed to a very high pressure, which can amount to from 10 to 100 bar. The test sieve 10 can withstand the said pressure by virtue of the underlying ancillary sieve 9 and of the plate 8 in the form of a sieve.

In front of the test sieve 10, a metal ring 11 is arranged. Once the test mixture has been—as far as is possible—practically entirely forced through the test sieve 10, the undispersed particles present in the test mixture finally remain in the region of the space 12 within the metal ring 11. That portion 13 of the specimen that remains within the space, i.e. the sieve cake, can easily be removed and tested. The size and thickness of the sieve cake 13 is then already suitable to permit inspection and analysis thereof under a microscope.

Figure 4:
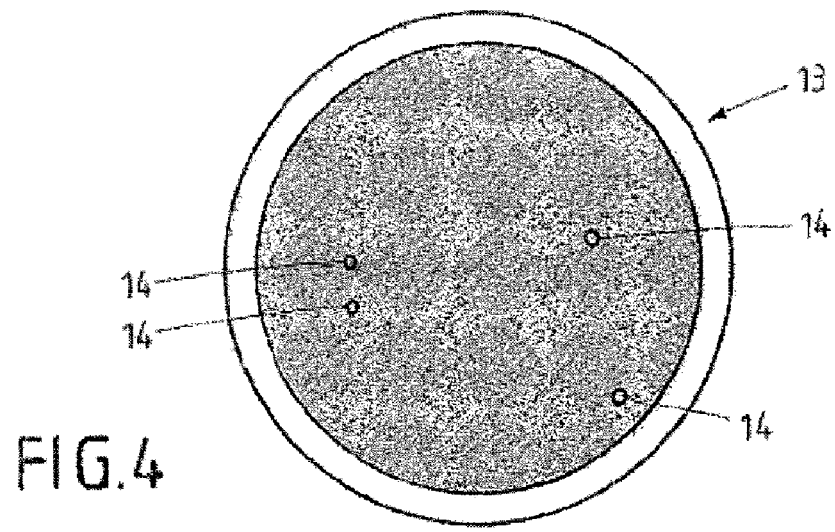
FIG. 4 schematically illustrates a material in accord with and produced by at least one embodiment of the present invention.

FIG. 4 illustrates a result obtained for a Rhenogran TBzTD-70. In the instance shown, one undispersed particle in category 1 with diameter from 150 to 175 µm was found, three undispersed particles in category 2 with diameter from 175 to 250 µm were found, and four undispersed particles 14, large enough to be discerned in FIG. 4, in category 3 with diameter more than 250 µm were found.

The test mixture was therefore defective, as therefore also was the polymer-bound rubber additive present in the mixture.

The test amounts used in the example were at least a total of 200 g and at most a total of 640 g. If other systems having different geometries are used, other amounts are also possible, for example if a larger cylinder is used.

According to the invention, the quantitative ratio used was 100 g of Rhenogran to be tested to 300 g of black EPDM masterbatch. The quantitative radio was therefore 1:3. However, other quantitative ratios are also possible, for example 1:2 or 1:4. If the concentration of Rhenogran® is excessive, errors can arise caused by an excessive number of undispersed particles which cannot then be evaluated by the operator because a deposit composed of undispersed particles has formed, thus rendering a counting procedure impossible. If the concentration of Rhenogran is too small, the number of undispersed particles occurring can be too small. If the number of undispersed particles is too small, the result may then lose its statistical relevance.

The present invention has been described with reference to specific details of particular embodiments thereof. It is not intended that such details be regarded as limitations upon the scope of the invention except insofar as and to the extent that they are included in the accompanying claims.

As used in this specification and the appended claims, the singular forms "a," "an," and "the" include plural referents unless the content clearly dictates otherwise.

What is claimed is:

1. A method for quality testing a polymer-bound rubber additive comprising the steps of:
   mixing the polymer-bound rubber additive with a test masterbatch to form a test mixture;
   forcing the test mixture through a test sieve thereby forming a filtered test-mixture fraction and a sieve cake faction, wherein the filtered test-mixture fraction is that portion of the test mixture that passes through the test sieve and wherein the sieve cake faction is that portion of the test mixture which does not pass through the test sieve and wherein said sieve cake faction comprises undispersed particles; and
   subsequently determining the number of undispersed particles in the sieve cake faction.

2. The method according to claim 1,
   wherein the forcing step is performed with the aid of a piston and a cylinder in which said piston is capable of moving within said cylinder and capable of applying a force to any substance within said cylinder so as to displace said substance from the cylinder, and
   wherein, said test sieve is positioned adjacent to said cylinder so as to receive and filter any substance forced through said cylinder via the piston, and
   wherein the test mixture is positioned within the cylinder and the piston applies force to the test mixture within the cylinder.

3. The method according to claim 2, further comprising:
   heating the test mixture prior to or during the mixing step, thereby forming a heated test mixture;
   prior to said forcing step, forming the heated test mixture into a shape capable of fitting within the cylinder, thereby forming a formed test mixture and inserting the formed test mixture into the cylinder.

4. The method according to claim 3, wherein the forming step is performed via the use of at least one roller.

5. The method according to claim 2, wherein a plurality of sieves and/or of plates are arranged adjacent to one another behind the test sieve, in relation to the direction of force being applied to any substance within the cylinder via the piston, and wherein the mesh size of each of the plurality of sieves increases in the direction of said force.

6. The method according to claim 5, wherein a ring is positioned in front of the test sieve, in relation to the direction of force.

7. The method according to claim 5, wherein the test sieve has a mesh width of not more than 150 µm and wherein the mesh widths of the plurality of sieves are greater than 150 µm.

8. The method according to claim 1, wherein said mixing step is performed via a double-roller system.

9. The process according to claim 1, wherein the test masterbatch is an EPDM masterbatch.

* * * * *